United States Patent [19]

Braun

[11] Patent Number: 5,468,256
[45] Date of Patent: Nov. 21, 1995

[54] SUBSTITUTE 4-{4'-{BIS-(B-HYDROXYETHYL)AMINO{PHENYLAZO{-BENZENESULFONIC ACID AMIDES AND HAIR DYE COMPOSITIONS CONTAINING SAME

[75] Inventor: Hans-Jürgen Braun, Ueberstorf, Switzerland

[73] Assignee: Wella Aktiengesellschaft, Darmstadt, Germany

[21] Appl. No.: 211,788

[22] PCT Filed: Jul. 6, 1993

[86] PCT No.: PCT/EP93/01734

§ 371 Date: April 15, 1994

§ 102(e) Date: April 15, 1994

[87] PCT Pub. No.: WO94/04123

PCT Pub. Date: March 3, 1994

[30] Foreign Application Priority Data

Aug. 19, 1992 [DE] Germany ............... 42 27 403.6

[51] Int. Cl.$^6$ ............... A61K 7/13; C09B 46/00
[52] U.S. Cl. ............ 8/405; 8/429; 8/552; 8/639; 8/666; 534/847
[58] Field of Search ............ 8/405, 552, 639, 8/667, 662, 683, 429, 641, 666, 682; 534/847

[56] References Cited

U.S. PATENT DOCUMENTS

| | | | |
|---|---|---|---|
| 3,050,516 | 8/1962 | Merian et al. ............ | 534/847 |
| 3,980,427 | 9/1976 | Neeff ............ | 8/681 |
| 4,315,857 | 2/1982 | Buecheler ............ | 534/847 |
| 4,886,517 | 12/1989 | Bugaut et al. ............ | 8/405 |
| 5,000,755 | 3/1991 | Anderson ............ | 8/405 |

FOREIGN PATENT DOCUMENTS

| | | |
|---|---|---|
| 3534885 | 10/1986 | Germany. |
| 1166906 | 10/1969 | United Kingdom. |
| 2165257 | 9/1986 | United Kingdom. |

OTHER PUBLICATIONS

"Dyes for Synthetic Fibers", Sanielevici et al., *Rev. Chim.* (1962)–See Abstract.
Chemical Abstracts, vol. 58, No. 1, Jan. 7, 1963.
J. C. Johnson, "Hair Dyes", 1973, pp. 3–91 and 113–139.
Colour Index, 3rd Edition, vol. 4, 1971, pp. 4070, 4389, 4390 and 4540.

*Primary Examiner*—Paul Lieberman
*Assistant Examiner*—Caroline L. Dusheck
*Attorney, Agent, or Firm*—Michael J. Striker

[57] ABSTRACT

The present invention includes new 4-{4'-{bis-(β-hydroxyethyl)amino}phenylazo}benzenesulfonic acid amides of formula (II)

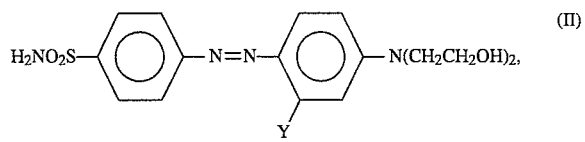

wherein Y is fluorine, chlorine or bromine. The invention also includes new hair dyeing compositions for dyeing hair including 0.01 to 5 percent by weight of the compound of formula II, 0.5 to 30 percent by weight of a surfactant and a solvent which can be water, ethanol, propanol, isopropanol, glycerin or 1,2-propylene glycol.

11 Claims, No Drawings

SUBSTITUTE 4-{4'-{BIS-(B-HYDROXYETHYL)AMINO {PHENYLAZO{-BENZENESULFONIC ACID AMIDES AND HAIR DYE COMPOSITIONS CONTAINING SAME

BACKGROUND OF THE INVENTION

The subject matter of the invention is a composition for dyeing hair containing a 4-[4' -[bis-(β-hydroxyethyl)amino] phenylazo]benzenesulfonic acid amide.

Along with oxidative hair dyes formed by the oxidative coupling of one or more developers, direct hair dyes are gaining increasing importance for dyeing hair. Direct hair dyes offer the advantage that they can be applied without the addition of oxidizing agents (for example, hydrogen peroxide) and therefore cause considerably less damage to the hair during the dyeing process.

Good hair dye compositions must satisfy a number of requirements. For example, they must create the desired tint or shade with sufficient intensity and at the same time be absorbed in the hair without excessive discoloration of the scalp. Further, the achieved color must possess sufficient fastness to light, heat, perspiration, hair cleaning agents, and chemicals used for permanent waving. They must also be stable with respect to the action of agents and diluted acids. Finally, these compositions should be unobjectionable in toxicological and dermatological respects.

Since a uniform coloring of the hair from the root to the tip of the hair is generally impossible with dyes from a single class of compounds, combinations of dyes from a number of different classes of compounds are normally used—for example, combinations of amino-, diamino-, or hydroxyamino-nitrobenzene derivatives with azo and anthraquinone dyes.

The most commonly used azo dye is 4'-amino-4-[bis-(β-hydroxyethyl)amino]azobenzene (DISPERSE BLACK 9). It is also known from DE-OS 35 34 885 to use 4' -amino-2-methyl-4-[bis-(β-hydroxyethyl)amino]azobenzene as a hair dye.

Although commonly used in hair dye compositions, the 4'-amino-4-[bis-(β-hydroxyethyl)amino]azobenzene is not completely satisfactory in technical respects relating to application. On the one hand, this compound is suspected of mutagenic behavior. On the other hand, colors produced by this compound and by the hair dyes known from DE-OS 35 34 885 have poor stability relative to acids and acidic preparations such as acidic hair rinses and shampoos, acid permanent wave compositions and fixing agents.

SUMMARY OF THE INVENTION

Therefore, it is an object of the present invention to provide hair dye compositions containing an azo dye which have good physiological compatibility and produce coloring which is stable with respect to acids and acidic preparations such as acidic hair rinses or hair cleaning agents, acidic permanent wave compositions and fixing agents and which therefore enable a long-lasting dyeing of hair which remains constant over longer periods of time.

It has now been found that this problem is solved in an outstanding manner by a composition for dyeing hair containing a 4-[4'-[bis(β-hydroxyethyl)amino]phenylazo]benzenesulfonic acid amide of the general formula (I).

The subject matter of the present invention is therefore a composition for dyeing hair containing conventional additives for hair dye compositions which is characterized in that it contains at least one 4-[4'-[bis-(β-hydroxyethyl)amino] phenylazo]benzenesulfonic acid amide of the general formula (I)

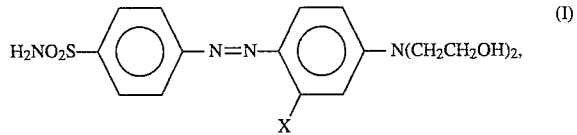

where X designates hydrogen, fluorine, chlorine, bromine, a $C_1$- to $C_3$-alkyl group or a $C_1$- to $C_3$-alkoxy group.

Of the compositions according to the invention, the composition containing 4-[4'-bis(β-hydroxyethyl)amino]phenylazo]benzenesulfonic acid amide of formula (I), where X designates hydrogen, fluorine, chlorine, methyl or methoxy, is preferred. The dyes of general formula (I) are contained in the composition according to the invention in concentrations of 0.01 to 5 percent by weight, preferably in concentrations of 0.01 to 2 percent by weight.

The hair dye according to the invention is a composition containing at least one dye of the general formula (I) or a composition containing one or more additional dyes which are direct dye compound absorbed directly in the hair, in addition to at least one dye of the general formula (I). Of these dyes which are absorbed directly in the hair, the following are mentioned by way of example: aromatic nitro dyes such as 2-amino-6-chloro-4-nitrophenol, 2-amino-4,6-dinitrophenol, 4-[(β-hydroxyethyl)amino]-2-nitroaniline, 2-chloro-6-ethylamino-4-nitrobenzene, $N^1$, $N^4$, $N^4$-tris(β-hydroxyethyl)-p-phenylenediamine (HC BLUE 2), 4-[bis-(β-hydroxyethyl)amino]-1-methylamino-2-nitrobenzene, 1-[(2,3-dihydroxypropyl)amino]-4-ethyl-[(2-hydroxyethyl)amino]-2-nitrobenzene, 1-[(2,3-dihydroxypropyl)amino]-4-dimethylamino-2-nitrobenzene, 1-[(2,3-dihydroxypropyl)-amino]-2-nitro-4-pyrrolidinobenzene, 4-[bis-(β-hydroxyethyl)amino]-1-[(3-hydroxypropyl)amino]-2-nitrobenzene, 2-amino-4-nitrophenol, 2-nitro-1,4-diaminobenzene, 2-amino-5-nitrophenol, 4-(β-hydroxyethyl)amino-3-nitrophenol, 1-(β-hydroxyethyl)amino-2-amino-4-nitrobenzene, 4-(β-ureidoethyl)aminonitrobenzene, 4-(2', 3'-dihydroxypropyl)amino-3 -nitrotrifluoromethylbenzene 1,4-bis[(β-hydroxyethyl)amino]-4-N-ethyl-2-nitrobenzene, 4-(β-hydroxyethyl)amino-3-nitrotoluene, 2,5-bis-[(β-hydroxyethyl)amino]nitrobenzene, 2-(β-hydroxyethyl)amino-4,6-dinitrophenol, 1-amino-4-(2',3'-dihydroxypropyl)amino-2-nitro-5-chlorobenzene, 1-amino-2-nitro-4-[bis-(β-hydroxyethyl)amino]benzene, triphenylmethane dyes, e.g. Basic Violet 1 (C.I. 42,535), Basic Violet 14 (C.I. 42,510), Basic Violet 2 (C.I. 42,520), azo dyes such as Acid Brown 4 (C.I. 14,805), anthraquinone dyes, e.g. 1-[(β-hydroxyethyl)amino]-4-methylamino anthraquinone (DISPERSE BLUE 3, C.I. 61,505), DISPERSE BLUE 23 (C.I. 61,545), 1,4-diaminoanthraquinone (DISPERSE VIOLET 1, C.I. 61,100), and 1,4,5,8-tetraaminoanthraquinone (C.I. 64,500). The dyes of these classes, depending on their constituents, can have an acidic, nonionic or basic character. Other suitable dyestuffs which are absorbed directly in the hair are described, for example, in J. C. Johnson, "Hair Dyes", Noyes Data Corp., Park Ridge, USA (1973), pages 3–91 and 113–139 (ISBN: 0-8155-0477-2).

The total amount of hair dye contained in the composition is preferably 0.01 to 8.0 percent by weight.

The preparation form of the hair dye composition described herein, which is also often called a tinting composition, can be a solution, particularly an aqueous or aqueous-alcoholic solution. Other preferred preparation forms are creams, gels, emulsions or foams. It can also be mixed with a propellant or sprayed by a pump.

The pH of this dye composition ranges from 3 to 12, particularly pH 8 to 11.5. The desired alkaline pH value is most often adjusted with ammonia, but this can also be done with organic amines such as monoethanolamine or triethanolamine.

The hair dye composition described here is usually used by applying an amount of this composition to the hair sufficient for dyeing the hair. The composition remains in contact with the hair for approximately 5 to 30 minutes. The hair is subsequently rinsed with water and, if necessary, also with an aqueous solution of weak organic acid, and is then rinsed and dried. Examples of such weak organic acids are acetic acid, citric acid, tartaric acid and the like.

The hair dye composition according to the invention can take the form of a hair dye composition with additional hair setting agents containing at least one polymerizate or natural polymer conventionally used in cosmetics. Such compositions are commonly known as tinting setting agents or color setting agents.

Of the polymerizates known for this purpose in cosmetics, the following are mentioned by way of example: polyvinylpyrrolidone, polyvinyl acetate, polyvinyl alcohol or polyacrylic compounds such as polyacrylic acid and polymethacrylic acid, basic polymerizates of the ester of polyacrylic acid or polymethacrylic acid with amino alcohols or their salts or quaternization products, polyacrylonitrile, polyvinyl lactams and copolymerizates of these compounds such as polyvinylpyrrolidone vinyl acetate and the like.

Natural polymers such as chitosan (deacetylated chitin) or chitosan derivatives can also be used for this purpose.

The polymerizates and natural polymers are contained in the hair dye composition described above in quantities usually used for such compositions, i.e. 1 to 5 percent by weight. The pH of the composition ranges from approximately 6.0 to 9.0. The use of this hair dye composition with additional setting agent is effected in a known and conventional manner by moistening the hair with the setting agent, setting the hair for styling, and subsequent drying.

If desired, the hair dye composition described above can, of course, also contain other conventional ingredients for hair dye compositions such as preservatives and perfume oils, solvents such as water, lower aliphatic alcohols, e.g. ethanol, propanol and isopropanol or glycols such as glycerin and 1,2-propylene glycol, and also wetting agents or emulsifiers from the classes of anionic, cationic, amphoteric or nonionic surface-active substances such as fatty alcohol sulfates, ethoxylated fatty alcohol sulfates, alkylsulfonates, alkylbenzenesulphates, alkyltrimethylammonium salts, alkyl betaines, ethoxylated fatty alcohols, ethoxylated nonylphenols, fatty acid alkanolamides, ethoxylated fatty acid esters, as well as thickeners such as higher fatty alcohols, starch or cellulose derivatives, petrolatum, paraffin oil and fatty acids, grooming materials such as cationic resins, tanolin derivatives, cholesterol, pantothenic acid and betaine. The ingredients mentioned above are contained in concentrations commonly used for such purposes, e.g. the wetting agents and emulsifiers in concentrations of 0.5 to 30 percent by weight, the thickeners in quantities of 0.1 to 25 percent by weight and the grooming materials in concentrations of 0.1 to 5.0 percent by weight.

The compounds of formula (I) contained in the hair dye compositions described herein are unobjectionable in toxicological and dermatological respects and achieve hair coloring with excellent stability with respect to acids and acidic preparations.

Depending on their type and the composition of the dye components, these hair dyes offer a wide range of different shades ranging from natural shades to highly-fashionable, brilliant hues.

The subject matter of this application also includes the new 4-[4'-[bis-(β-hydroxyethyl)amino]phenylazo]benzenesulfonic acid amides of formula (II)

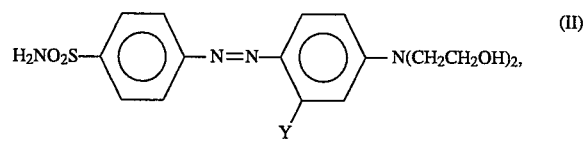

where Y is fluorine, chlorine, bromine, a $C_2$- to $C_3$-alkyl group or a $C_1$- to $C_3$-alkoxy group.

The following compounds of formula (II) are mentioned in particular:

4-[4'-[bis-(β-hydroxyethyl)amino]-2'-methoxyphenylazo]benzenesulfonic acid amide, 4-[4'-[bis-(β-hydroxyethyl)amino]-2'-fluorophenylazo]benzenesulfonic acid amide, 4-[4'-[bis-(β-hydroxyethyl)amino]-2'-chlorophenylazo]benzenesulfonic acid amide, 4-[4'-[bis-(β-hydroxyethyl)amino]-2'-ethylphenylazo]benzenesulfonic acid amide, As with the compounds of formula (I), these new compounds of formula (II) can be produced in a single step according to the following reaction equation (Y=F, Cl, Br, $C_2$- to $C_3$-alkyl or $C_1$- to $C_3$-alkoxy):

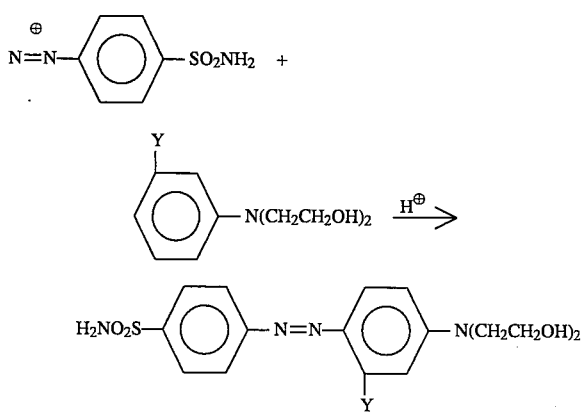

The production process is carried out as follows:

An aqueous solution of the diazonium salt of 4-aminobenzenesulfonic acid amide is added by drops to an equimolar amount of the corresponding 3 position substituted N,N-(β-hydroxyethyl)aniline accompanied by cooling. The reaction mixture is then stirred for 24 hours at room temperature and subsequently neutralized with ammonia.

The obtained precipitate is removed by filtration, washed in water and dried over calcium chloride.

To produce the hydrochlorides, the compounds of formula (II) are dissolved in ethanol and mixed with a trimolecular hydrochloric acid. The hydrochlorides are then precipitated out of the reaction mixture with diethyl ether.

The following examples will explain the subject matter of the present invention in more detail without limiting the invention to these examples.

PRODUCTION EXAMPLES

Example 1 to 4

Production of 4-[4'-[bis-(β-hydroxyethyl)amino]phenylazo]benzenesulfonic acid amides of formula (I)

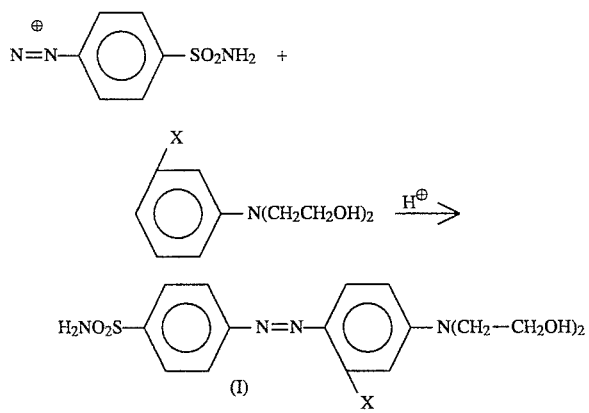

6.9 g (0.04 moles) 4-aminobenzenesulfonic acid amide are diazotized in a mixture of 20 g water, 60 g crushed ice, and 6.8 ml concentrated hydrochloric acid with 3.0 g (0.044 moles) sodium nitrite at 0° C. The obtained solution of diazonium salt is filtered and the filtrate is added by drops within one hour accompanied by stirring to a cooled solution of 0.04 moles of the corresponding 3-position-substituted N,N-bis-(β-hydroxyethyl)aniline in 32 ml water and 6.8 ml concentrated hydrochloric acid.

The reaction mixture is then stirred for 24 hours at room temperature and neutralized with ammonia (pH=7.5). The precipitated azo compound is filtered out, washed with water and dried over calcium chloride.

To produce the hydrochlorides, the benzenesulfonic acid amides of formula (I) are dissolved in ethanol and mixed with 3-molar HCl. The hydrochlorides are then preciptated with diethyl ether.

The following reaction products are obtained:

Example 1

4-[4'-[bis-(β-hydroxyethyl)amino]-2'-ethylphenylazo]benzenesulfonic acid amide

Yield: 13.6 g (87% of theory)
Melting point: 196° to 197° C. (red, crystalline powder)
CHN analysis: $(C_{18}H_{24}N_4O_4S)$

| (MG = 392.48) | % C | % H | % N |
|---|---|---|---|
| estimated: | 55.09 | 6.16 | 14.28 |
| actual: | 54.86 | 6.04 | 14.03 |

Example 2

4-[4'-[bis-(β-hydroxyethyl)amino]-2'-methoxyphenylazo]benzenesulfonic acid amide hydrochloride Yield: 6.0 g (35% of theory)
Melting point: 86° to 89° C. accompanied by decomposition (dark-brown powder)
CHNCl analysis: $(C_{17}H_{22}N_4O_5S \times HCl)$

| (MG = 430.91) | % C | % H | % N | % Cl |
|---|---|---|---|---|
| estimated: | 47.38 | 5.38 | 13.00 | 8.23 |
| actual: | 46.58 | 5.45 | 11.85 | 6.72 |

Example 3

4-[4'-[bis-(β-hydroxyethyl)amino]-2'-fluorophenylazo]benzenesulfonic acid amide

Yield: 8.8 g (53% of theory)
Melting point: 173° to 175° C. (orange powder)
CHNS analysis: $(C_{16}H_{19}FN_4O_4S)$

| (MG = 418.87) | % C | % H | % N | % S |
|---|---|---|---|---|
| estimated: | 50.25 | 5.01 | 14.65 | 8.38 |
| actual: | 49.27 | 5.13 | 13.81 | 8.10 |

Example 4

4-[4'-[bis-(β-hydroxyethyl)amino]-2'-chlorophenylazo]benzenesulfonic acid amide hydrochloride Yield: 10.8 g (68% of theory)
Melting point: 181° to 183° C. accompanied by decomposition (dark-red powder)
CHNCl analysis: $(C_{16}H_{19}ClN_4O_4S \times HCl)$

| (MG = 398.86) | % C | % H | % N | % Cl |
|---|---|---|---|---|
| estimated: | 44.15 | 4.63 | 12.87 | 16.29 |
| actual: | 44.25 | 4.40 | 12.94 | 13.38 |

Example 5

4-[4'-[bis-(β-hydroxyethyl)amino]phenylazo]benzenesulfonic acid amide hemihydrate Yield: 9.7 g (65% of theory)
Melting point: 181° to 183° C. (orange flakes)
CHNS analysis: $(C_{16}H_{20}N_4O_4S \times \frac{1}{2}H_2O)$

| (MG = 373.43) | % C | % H | % N | % S |
|---|---|---|---|---|
| estimated: | 51.46 | 5.67 | 15.00 | 8.59 |
| actual: | 51.53 | 5.56 | 14.71 | 8.59 |

Example 6

4-[4'-[bis-(β-hydroxyethyl)amino]phenylazo]benzenesulfonic acid amide hydrochloride Melting point: 185° to 186° C. accompanied by decomposition (red powder) CHNCl analysis: $(C_{16}H_{20}N_4O_4S \times HCl)$

| (MG = 400.88) | % C | % H | % N | % Cl | % S |
|---|---|---|---|---|---|
| estimated: | 47.94 | 5.28 | 13.98 | 8.84 | 8.00 |
| actual: | 47.21 | 5.17 | 13.39 | 9.06 | 7.81 |

Example 7

4-[4'-[bis-(β-hydroxyethyl)amino]-2'-methylphenylazo] benzenesulfonic acid amide hydrochloride Yield: 12.4 g (75% of theory)

Melting point: 95° to 98° C. accompanied by decomposition (brown powder)

CHNCl analysis: ($C_{17}H_{22}N_4O_4S \times HCl$)

| (MG = 414.91) | % C | % H | % N | % Cl |
|---|---|---|---|---|
| estimated: | 49.21 | 5.59 | 13.50 | 8.54 |
| actual: | 48.30 | 5.65 | 12.75 | 7.84 |

Examples for hair dye compositions:

Example 8

Hair dye solution

| | |
|---|---|
| 0.3g | 4-[4'-[bis-(β-hydroxyethyl)amino]phenylazo]benzene-sulfonic acid amide of the general formula (I) |
| 2.0g | lauryl alcohol diglycol ether sulfate sodium salt (28-percent aqueous solution) |
| 2.0g | ammonia (25-percent aqueous solution) |
| 10.0g | isopropanol |
| 85.7g | water |
| 100.0g | |

Bleached human hair is treated for 20 minutes at room temperature with this hair dye solution. The hair is then rinsed with water and dried. The hair is dyed as indicated in Table 1.

TABLE 1

Hair dyes

| 4-[4'-[bis-(β-hydroxyethyl)amino]phenylazo]benzene-sulfonic acid amide of formula (I) | hair color |
|---|---|
| 4-[4'-[bis-(β-hydroxyethyl)amino]-2'-fluoro-phenylazo]-benzenesulfonic acid amide, | orange |
| 4-[4'-[bis-(β-hydroxyethyl)amino]-2'-chloro-phenylazo]-benzenesulfonic acid amide hydrochloride, | orange |
| 4-[4'-[bis-(β-hydroxyethyl)amino]-2'-ethyl-phenylazo]-benzenesulfonic acid amide | orange |
| 4-[4'-[bis-(β-hydroxyethyl)amino]-2'-methoxy-phenylazo]-benzenesulfonic acid amide, | red-orange |
| 4-[4'-[bis-(β-hydroxyethyl)amino]-2'-methyl-phenylazo]-benzenesulfonic acid amide | bright red |

Example 9

Hair dye cream

| | |
|---|---|
| 0.04 g | 4-[4'-[bis-(β-hydroxyethyl)amino]phenylazo]benzene-sulfonic acid amide hemihydrate |
| 0.30 g | $N^1,N^4,N^4$-tris-(β-hydroxyethyl)-2-nitro-p-phenylene-diamine |
| 0.03 g | 1-nitro-4-[2-ureidoethyl)amino]benzene |
| 0.02 g | Disperse Blue 3 (C.I. 61,505) |
| 0.02 g | Disperse Violet 1 (C.I. 61,100) |
| 0.02 g | 4-[(2-hydroxyethyl)amino]-2-nitroaniline |
| 7.00 g | cetyl alcohol |
| 2.00 g | lauryl alcohol diglycol ether sulfate sodium salt (28-percent aqueous solution) |
| 0.20 g | ammonia (25-percent aqueous solution) |
| 0.10 g | p-hydroxybenzoic acid methyl ester |
| 90.27 g | water |
| 100.0 g | |

50 g of the preceding hair dye composition are applied to white human hair, allowed to act for 20 minutes, and rinsed out with water.

The hair is then dried. The hair treated in this way is dyed a natural brown shade.

Example 10

Hair dye solution

| | |
|---|---|
| 0.05 g | 4-[4'-[bis-(β-hydroxyethyl)amino]-2'-chlorophenylazo]-benzenesulfonic acid amide hydrochloride |
| 0.05 g | 1,4-diaminoanthraquinone |
| 0.10 g | $N^1,N^4,N^4$-tris-(β-hydroxyethyl)-2-nitro-p-phenylene-diamine |
| 0.50 g | hydroxyethyl cellulose |
| 5.00 g | lauryl alcohol diglycol ether sulfate sodium salt (28-percent aqueous solution) |
| 10.00 g | ammonia (25-percent aqueous solution) |
| 10.00 g | isopropanol |
| 74.30 g | water |
| 100.0 g | |

Bleached natural human hair is treated for 20 minutes at room temperature with the hair dye solution of the preceding composition. The hair is then rinsed with water and washed with a shampoo. After drying, the hair has an ash-blond color.

Example 11

Comparison tests for resistance to acids

To compare the stability toward acids possessed by the 4-[4'-[bis-(β-hydroxyethyl)amino]phenylazo]-benzene-sulfonic acid amides, according to the invention, with that of the 4'-amino-4-[bis-(β-hydroxyethyl)amino]azobenzenes known from the prior art, strands of natural hair were dyed as described in Example 8 using the following hair dye compositions:

(i) a composition according to Example 8 in which the 4-[4'-[bis-(β-hydroxyethyl)amino]phenylazo]benzene-sulfonic acid amides, according to the invention, were replaced with an equal amount of 4'-amino-4-[bis-(β-hydroxyethyl)amino]azobenzene, (ii) a composition according to Example 8 (compound according to Table 2 with X=H; R=SO₂NH₂), (iii) a composition according to Example 8 (compound according to Table 2 with X=CH₃; R=SO₂NH₂), (iv) a composition according to Example 8 (compound according to Table 2 with X=OCH₃; R=SO₂NH₂), (v) a composition according to Example 8 (compound according to Table 2 with X=F; R=SO₂NH₂), (vi) a composition according to Example 8 (compound according to Table 2 with X=Cl; R=SO₂NH₂), (vii) a composition according to Example 8 (compound according to Table 2 with X=C₂H₅; R=SO₂NH₂), The strands of hair which were dyed in this way were subsequently treated with 1n-hydrochloric acid for 1 minute and then washed with an acidic shampoo (pH=5.5) and dried.

The laboratory color values of the hair strands dyed in this way were determined by a Minolta color measurement device, Type CR-200. The determined laboratory color values are compiled in the following table:

TABLE 2

Color measurement values of washing tests with 1n-hydrochloric acid

R—⟨○⟩—N=N—⟨○⟩—N(CH₂CH₂OH)₂
                    |
                    X

| R | X | not treated | 1n-hydrochloric acid |
|---|---|---|---|
| (i) NH₂ | H | L 58.8 | 37.5 |
|  |  | a 41.7 | 6.0 |
|  |  | b 77.3 | 38.1 |
| (ii) SO₂NH₂ | H | L 58.1 | 63.4 |
|  |  | a 38.1 | 38.4 |
|  |  | b 67.1 | 74.0 |
| (iii) SO₂NH₂ | CH₃ | L 53.2 | 56.4 |
|  |  | a 54.0 | 54.8 |
|  |  | b 61.6 | 64.4 |
| (iv) SO₂NH₂ | OCH₃ | L 54.5 | 58.4 |
|  |  | a 52.3 | 51.3 |
|  |  | b 61.2 | 65.4 |
| (v) SO₂NH₂ | F | L 64.6 | 66.0 |
|  |  | a 37.0 | 34.9 |
|  |  | b 78.6 | 80.8 |
| (vi) SO₂NH₂ | Cl | L 53.2 | 58.0 |
|  |  | a 49.6 | 48.4 |
|  |  | b 62.1 | 69.4 |
| (vii) SO₂NH₂ | C₂H₅ | L 63.5 | 66.1 |
|  |  | a 30.8 | 36.8 |
|  |  | b 56.2 | 51.7 |

Table 2 shows that the measured color values of the strands of hair treated with the composition (ii–vii) according to the invention are reduced substantially less when treated with acids than the strands of hair treated with the known compound (i).

The substantially improved stability toward acid of the hair dye composition according to the invention compared to the prior art is even more apparent when the total change in color Δ Y is calculated according to Anderson (cf. U.S. Pat. No. 5,000,755) based on the following equation:

$$\Delta Y = \sqrt{(\Delta L)^2 + (\Delta b)^2}$$

The values determined for the total change in color Δ Y are compiled in Table 3;

TABLE 3

Total change in color ΔY

R—⟨○⟩—N=N—⟨○⟩—N(CH₂CH₂OH)₂
                    |
                    X

| R | X | 1n-hydrochloric acid |
|---|---|---|
| (i) NH₂ | H | 57.1 |
| (ii) SO₂NH₂ | H | 8.7 |
| (iii) SO₂NH₂ | CH₃ | 4.3 |
| (iv) SO₂NH₂ | OCH₃ | 5.8 |
| (v) SO₂NH₂ | F | 3.3 |
| (vi SO₂NH₂ | Cl | 8.8 |
| (vii) SO₂NH₂ | C₂H₅ | 7.9 |

The strands of hair treated with the composition according to the invention (ii–vii) show a substantially smaller total change in color (Δ Y) when acted upon by 1n-hydrochloric acid than the hair strands treated with the known composition (i).

All percentages represent percent by weight unless otherwise indicated.

I claim:

1. Composition for dyeing hair containing at least one solvent selected from the group consisting of water, ethanol, propanol, isopropanol, glycerin and 1,2-propylene glycol; 0.5 to 30 percent by weight of at least one anionic, cationic and nonionic surface-active substance and 0.01 to 5 percent by weight at least one 4-[4'-[bis-(β-hydroxyethyl)amino]-phenylazo]benzenesulfonic acid amide of the formula (I)

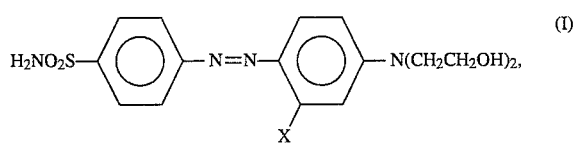

wherein X is selected from the group consisting of fluorine, chlorine and bromine.

2. Composition according to claim 1, wherein in said 4-[4'-bis-(β-hydroxyethyl)amino]phenylazo]benzene-sulfonic acid amide of said formula (I) said X is selected from the group consisting of said fluorine and said chlorine.

3. Composition according to claim 1, having a pH of 3 to 12.

4. Composition according to claim 1, in the form of an aqueous of aqueous-alcoholic solution, a cream, a gel, an emulsion or a foam.

5. Composition according to claim 1, further comprising at least one direct hair dye compound.

6. Composition according to claim 5, wherein the at least one direct hair dye compound is selected from the group consisting of 2-amino-6-chloro-4-nitrophenol, 2-amino-4,6-dinitrophenol, 4-[(β-hydroxyethyl)amino]-2-nitroaniline, 2-chloro-6-ethylamino-4-nitrobenzene, N¹, N⁴, N⁴-tris-(β-hydroxyethyl)-p-phenylenediamine, 4-[bis-(β-hydroxyethyl)amino]-1-methylamino-2-nitrobenzene, 1-[(2,3-dihydroxypropyl)amino]-4-ethyl-[(2-hydroxyethyl)amino]-2-nitrobenzene, 1-[(2,3-dihydroxypropyl)amino]-4-dimethylamino-2-nitrobenzene, 1-[(2,3-dihydroxypropyl)amino]-2-nitro-4-pyrrolidinobenzene, 4-[bis-(β-hydroxyethyl)amino]-1-[(3-hydroxypropyl)amino]-2-nitrobenzene, 2-amino-4-nitrophenol, 2-nitro-1,4-diaminobenzene, 2-amino-5-nitrophenol, 4-(β-hydroxyethyl)amino-3-nitrophenol, 1-(β-hydroxyethyl)amino-2-amino-4-nitrobenzene, 4-(β-ureidoethyl)aminonitrobenzene, 4-(2',3'-dihydroxypropyl)-amino-3-nitrotrifluoromethylbenzene, 1,4-bis-[(β-hydroxyethyl)aminol-4-N-ethyl-2-nitrobenzene, 4-(β-hydroxyethyl)amino-3-nitrotoluene, 2,5-bis-[(β-hydroxyethyl)amino]nitrobenzene, 2-(β-hydroxyethyl)amino-4,6-dinitrophenol, 1-amino-4-(2',3'-dihydroxypropyl)amino-2-nitro-5-chlorobenzene, 1-amino-2-nitro-4-[bis-(β-hydroxyethyl)amino]benzene, mixtures of N-tetra, N-penta and N-hexamethylated 4-{(4'-aminophenyl)-(4"-imino-2",5"-cyclohexadiene-1"-yliden)methyl}aminobenzene hydrochloride (Basic Violet 1), 4-{(4'-aminophenyl)-(4"-imino-2",5"-cyclo-hexadien-1"-yliden)-methyl}2-methylaminobenzene monohydrochloride (Basic Violet 14), 4-}(4'-amino-3'-methylphenyl)-(4"-imino-3"-methyl-2",5"-cyclohexadiene-1"-yliden)methyl-2-methylaminobenzene monohydrochloride (Basic Violet 2), 7-{(4'-aminophenyl)azo}-8-hydroxynaphthalene-4-sulfonic acid sodium salt (Acid Brown 4), 1-[(β-hydroxyethyl)amino]-4-methylaminoanthraquinone, 1,4-di(2-hydroxyethylamino)-anthraquinone (Disperse Blue 53), 1,4-diaminoanthraquinone and 1,4,5,8-tetraaminoanthraquinone.

7. Composition according to claim 1, further comprising at least one hair setting agent and at least one polymer member selected from the group consisting of chitosan, chitosan derivatives, polyacrylonitrile, polyvinyl lactams and copolymerizates of said polyvinyl lactams, polyvinylpyrrolidone, polyvinyl acetate, polyvinyl alcohol, and polyacrylic compounds.

8. Composition according to claim 1, further comprising at least one ingredient selected from the group consisting of preservatives, perfume oils, thickeners and grooming materials.

9. 4-[4'-[Bis-(β-hydroxyethyl)amino]phenylazo]benzenesulfonic acid amides of formula (II)

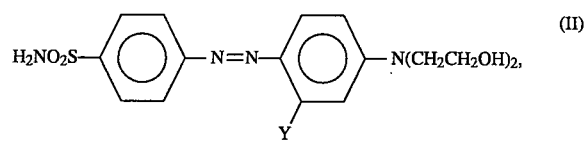

wherein Y is selected from the group consisting of fluorine, chlorine and bromine.

10. 4-[4'-[Bis-(β-hydroxyethyl)amino]-2'-fluorophenylazo]benzenesulfonic acid amide.

11. 4-[4'-[Bis-(β-hydroxyethyl)amino]-2'-chlorophenylazo]benzenesulfonic acid amide.

* * * * *